United States Patent [19]
Davison

[11] Patent Number: 5,834,633
[45] Date of Patent: Nov. 10, 1998

[54] DEVICE FOR CONCENTRATING TRACE COMPONENTS IN A LIQUID

[75] Inventor: William Davison, Windermere, United Kingdom

[73] Assignee: University of Lancaster, Lancaster, United Kingdom

[21] Appl. No.: 591,636

[22] PCT Filed: Aug. 12, 1994

[86] PCT No.: PCT/GB94/01775

§ 371 Date: Feb. 12, 1996

§ 102(e) Date: Feb. 12, 1996

[87] PCT Pub. No.: WO95/05591

PCT Pub. Date: Feb. 23, 1995

[30] Foreign Application Priority Data

Aug. 14, 1993 [GB] United Kingdom .................. 9316945

[51] Int. Cl.[6] .............................. G01N 1/40; G01N 30/00; G01N 33/18
[52] U.S. Cl. ...................... 73/53.01; 73/61.41; 73/64.56; 73/863.23; 73/864.51; 210/638; 210/653; 210/688; 210/490
[58] Field of Search ............................... 73/53.01, 61.41, 73/64.56, 863.21, 863.23, 864, 864.51; 210/490, 638, 653, 688

[56] References Cited

U.S. PATENT DOCUMENTS

| | | | |
|---|---|---|---|
| 3,817,379 | 6/1974 | Zipilivan et al. | 210/94 |
| 3,922,432 | 11/1975 | Renn | 210/635 X |
| 4,092,117 | 5/1978 | Byrne | 436/178 X |
| 4,584,246 | 4/1986 | Liu et al. | 210/500.34 X |
| 4,786,597 | 11/1988 | Matson et al. | 210/638 X |
| 4,976,866 | 12/1990 | Grinstead et al. | 210/638 |

OTHER PUBLICATIONS

Audunsson, "Aqueous/Aqueous Extraction by Means of a Liquid Membrane For Sample Cleanup and Preconcentration of Amines in a Flow System", Analytical Chemistry, vol. 58, No. 13, Nov. 1986, pp. 2714–2723.

Beneš, "Semicontinuous Monitoring of Truly Dissolved Forms of Trace Elements in Streams Using Dialysis In Situ—I. Principles and Conditions", Water Research, vol. 14, 1986, pp. 511–513.

Davison et al., "Distribution of Dissolved Iron in Sediment Pere Waters at Submillimetre Resolution", Nature, vol. 352, 25 Jul. 1991, pp. 323–325.

Davison et al., "In Situ Speciation Measurements of Trace Components in Natural Waters Using Thin–Film Gels", Nature, vol. 367, 10 Feb. 1994, pp. 546–548.

Primary Examiner—Hezron E. Williams
Assistant Examiner—Daniel S. Larkin
Attorney, Agent, or Firm—Woodard, Emhardt, Naughton, Moriarty & McNett

[57] ABSTRACT

A probe device for use in measuring trace quantities of a component in a liquid environment comprises: (i) a membrane which is permeable to the component; and (ii) a layer of a material capable of binding the component and arranged to receive material which has permeated through the membrane from a face thereof juxtaposed to the fluid environment. The membrane may, for example, be a polyacrylamide gel and the material an ion exchange resin. The device may be used, for example, for determining quantities of trace metals in an aqueous environment.

25 Claims, 4 Drawing Sheets

DEVICE FOR CONCENTRATING TRACE COMPONENTS IN A LIQUID

The present invention relates to a probe for use in measuring amounts of a component in a liquid environment, e.g. for use in measuring trace metal concentrations. The invention relates more particularly but not exclusively to such a device for use in an aqueous environment (e.g. river, lake, sea etc).

The idea of using a passive in situ sampling device to provide an integrated record of trace metal concentrations in natural waters has long appealed to regulatory authorities. To date, this role has been partly filled by analysis of the metal content of shellfish such as mussels.

It has been proposed to use Chelex resin in situ to concentrate a wide range of metal ions from natural waters. For example the resin has been suspended in a bag but the mass transport of ions to the resin has been ill defined resulting in at best semi-quantitative data. To overcome this problem, water has been mechanically pumped over the resin but such procedures are inevitably complicated, expensive and cumbersome.

Recently polyacrylamide gels have been used to provide measurements of metal ion concentrations in pore waters by the technique of diffusive equilibration in thin films (DET) —see Nature, Vol 352, pages 323–325 (Jul. 25, 1991). In this technique, ions are simply allowed to diffuse into the gel until equilibrium with the pore waters is established. The gel can then be analysed by techniques such as a proton microprobe or MeV-proton-induced X-ray emission (PIXE) to determine trace metal amounts at submillimetre resolution. The article in Nature states that detection limits could possibly be lowered by incorporating chemical concentration steps within the gel but there is no further disclosure as to this possibility.

According to a first aspect of the present invention there is provided a probe device for use in measuring quantities of a component in a liquid environment, the device comprising means providing a diffusion pathway which is or which contains a liquid, and along which said component may diffuse, and a layer of a material in contact with the diffusion pathway and arranged to receive component which has diffused along said pathway from a face of the device juxtaposed, in use of the device, to said liquid environment, said diffusion pathway having a length of at least 0.1 mm.

In use, the device is located in the liquid environment and the component to be measured diffuses along the diffusion pathway until it reaches the material which is capable of binding the component. It can be shown (see infra) that this results in a large concentration enhancement of the component in the material as compared to that in the liquid environment. After a suitable period of immersion, the device (which will generally be used only once) may be retrieved and the material analysed to determine the amount of the component present therein. This may be related to the amount of the component present in the liquid environment as described more fully below.

Therefore according to a second aspect of the present invention there is provided a method of determining the amount of a component present in a liquid environment comprising providing the device of the first aspect of the invention in the liquid environment and subsequently analysing said material to determine the amount, or a representation of the amount, of said component therein.

The device is particularly useful for determining amounts of components (e.g. metal ions) in aqueous environments. The liquid which is, or which is contained within, the diffusion pathway is preferably water.

When a device in accordance with the invention is immersed in a liquid environment a diffusive boundary layer (DBL) is established at the device/liquid environment interface. It is an important feature of the invention that, as explained later, the length of the diffusion pathway is greater (preferably by a factor of at least 10, more preferably at least 20) than the thickness of the DBL. This thickness does depend on the liquid environment in which the device is located and is greater, for example, for stagnant bodies of water than for a flowing stream or river. In all cases, a device in accordance with the invention will have a diffusion pathway having a length of at least 0.1 mm. However a device having a diffusion pathway of a particular length may be suitable for use in a stream or river but not in a stagnant body of water. FIG. 8 below illustrates a technique for determining effective mean thickness of the DBL thickness.

A particular feature of the device in addition to the concentration enhancement mentioned above is that (provided the diffusion pathway is of a length substantially greater than the DBL thickness) the diffusion pathway controls the mass transfer and rate of transport of the component to the binding material irrespective of changes in the velocity of the liquid in the environment.

Provided that the thickness of the DBL is substantially less than the length of the diffusion pathway then the concentration of the component in the liquid environment can be calculated according to equation (4) below. This provides a means of testing whether a particular length of diffusion pathway is sufficiently greater than the DBL thickness. Thus, if it is desired to determine what length of diffusion pathway is required for a particular liquid environment, a number of devices each having diffusion pathways of different length may be immersed in the liquid environment for the same length of time. The devices are then analysed to determine the amount of component in the liquid environment. Those devices which give essentially the same results will have diffusion pathways of sufficient length for that environment.

The diffusion pathway may be provided in a number of ways such that only molecular diffusion takes place. In accordance with a preferred aspect of the invention the diffusion pathway is provided by a porous membrane which contains water. The membrane may comprise a water-containing gel, e.g. a polyacrylamide gel. Alternatively, the membrane may be of a material which is readily hydrated to provide the liquid for the diffusion pathway.

The material (for binding the component) may be a particulate material and may be incorporated in the membrane or provided as a separate layer juxtaposed thereto. For example, in the case where the membrane is a gel, the material may be incorporated in the membrane or may be provided in a further gel layer juxtaposed to the membrane.

If required, a filter or the like may be provided over that face of the membrane which is juxtaposed to the liquid environment so as to prevent fouling of the membrane by contaminants in the liquid environment.

In an alternative embodiment of the invention, the device may incorporate a solid member (e.g. a disk of plastics material) provided with apertures of relatively small cross-section (e.g. 0.1 to 2 mm, more particularly about 0.5 mm). The apertures (provided through the thickness of the member) are filled with liquid (e.g. water) and provide the diffusion pathway. The member is sandwiched between the material for binding the component and a front filter (required to retain the liquid in the holes). Because the apertures are so small and liquid movement is prevented at each end of the holes, there is no convection within the aperture and only molecular diffusion applies. The total cross-sectional area of the aperture is only a fraction of the total area of the member. This can be used advantageously in solutions of high concentration to reduce the sensitivity of the device. In this way, longer exposure times may be tolerated before the binding material becomes saturated.

Whatever the construction of the device, it is important to ensure that air bubbles are not trapped at any point in the assembly. If air bubbles are trapped then, no matter how small, they will prevent free diffusion at that point.

The diffusion pathway has a length (which equates to the thickness of the membrane or the length of the aforementioned passageways) of at least 0.1 mm. There is no particular upper limit on the length of the pathway other than that governed by the overall size of the device. Typically the pathway will have a length of up to 10 mm, more preferably up to 5 mm. Preferred devices in accordance with the invention have a diffusion pathway having a length in the range 0.2 mm to 5 mm, e.g. 0.4 to 2.5 mm.

The binding layer may for example be of a particulate material and may have a thickness of 10–1000 microns, e.g. 10–200 microns.

A particular use of the device is for determining the concentration of a trace metal ion or ions in an aqueous environment (e.g. river, lake, sea etc). For this purpose it is preferred that the material for binding the ion(s) is an ion exchange resin (e.g. Chelex). It is however also possible for the device to be used for determining amounts of other types of components in the liquid environment, e.g. anions, cations or organic compounds such as pesticides. Appropriate binding materials would be cation and anion exchange materials for binding of anions and cations respectively, hydrous iron oxides for binding phosphate, and adsorbents (e.g. $C_{18}$ or charcoal) for organic material (e.g. pesticides) to be bound. Alternatively the material may comprise an immobilised complexing agent. Ions being measured may be radioactive and the binding material may be specific for the ion concerned, e.g. potassium hexacyano cobalti ferrate for caesium and Duolite A378, a strong quaternary base exchanger, for technetium.

The device of the invention makes a speciation measurement. It measures labile species in solution. Thus, in the case of metal ions, it measures the free metal ion and those metal ligand complexes which can dissociate in the time which it takes to diffuse along the diffusion pathway. It therefore defines the measured species kinetically which is a significant difference over the device described in the aforementioned article in Nature which requires equilibration of the species and hence defines the species thermodynamically.

Speciation depends on the solution. Thus some natural waters in which the device of the invention may be used will have metals present as free ions or simple labile complexes and all of the metal will be measured. In other situations, there will be inert complexes which will not be measured. The device of the invention may therefore be used for measuring an operationally defined labile metal fraction. This labile fraction represents the chemically reactive fraction and is likely to be similar to the fraction which is available to living organisms.

The invention will be further described by way of example only with reference to the accompanying drawings in which FIG. 1 is a schematic view illustrating the principle of the invention, and FIG. 1a shows an enlargement of a portion of the particulate ion exchange resin;

Figure 1A:
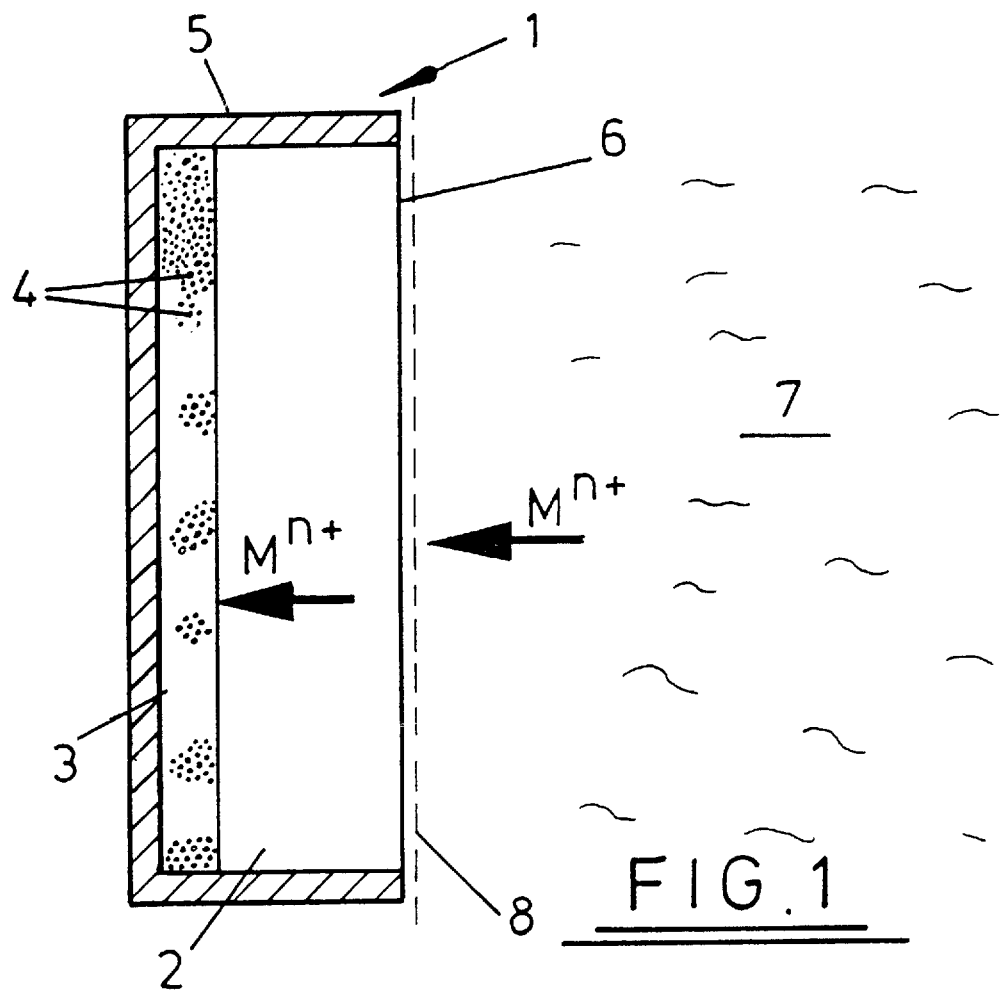
Figure 1A:
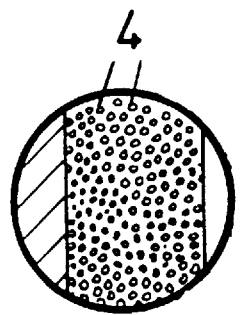

FIG. 1 schematically illustrates to a much enlarged scale a probe device 1 which comprises a layer 2 of an ion permeable gel (e.g. a polyacrylamide gel) backed by a further gel layer 3 including closely spaced (e.g. close packed) particulate ion exchange resin 4 (e.g. a Chelex resin such as Chelex 100). The device further includes an outer liquid impermeable barrier 5 which encloses the layers 2 and 3 save for face 6 of the latter, i.e. that face remote from layer 3.

Depending on the usage, layer 2 will have a thickness of typically 0.1 mm to 5 mm whereas layer 3 will be generally in the range 10 to 1000 microns. The ion exchange resin will typically have a particle size of 1–200 microns.

Device 1 is shown as being immersed in an aqueous liquid 7 containing trace quantities of a metal ion ($M^{n+}$). Liquid 7 is shown as establishing a diffusive boundary layer 8 at the face 6 of layer 2. The gel layer will be of significantly greater thickness than diffusive boundary layer 8.

Ions $M^{n+}$ are able to diffuse across the diffusive boundary layer 8 and gel membrane 2 to the ion exchange resin layer 3 where (for the reasons given below) their concentration in the solid phase as bound to the resin becomes significantly greater than the concentration in the bulk liquid. The concentration of the ions in the resin may then be measured and, having regard to the principles outlined below, used to calculate the concentrations of $M^{n+}$ in the bulk liquid.

Figure 2:
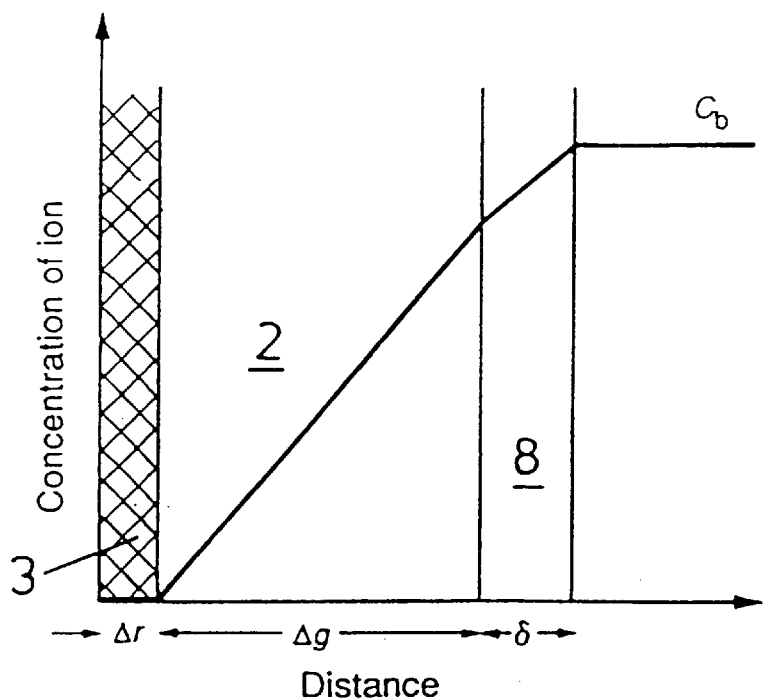
FIG. 2 is a graph illustrating use of the device shown in FIG. 1.

The manner in which the significant increase in concentration of the metal ion in the resin occurs is explained below, and is shown graphically in FIG. 2.

Within the layer of resin, of thickness Δr, the concentration of the free metal in solution is effectively zero due to the complexation of the resin. Within the bulk liquid 7 the metal has a concentration $C_b$. To be transported from the solution to the resin, ions must diffuse across the diffusive boundary layer 8, of thickness δ, and then through the gel layer 2, of thickness Δg. Ions can diffuse freely through the gel layer 2 with effective diffusion coefficients (D) approximately equal to the molecular values (unpublished results). If, for simplicity, it is assumed that δ<<Δg Fick's laws can be used to define the flux of a given metal ion $$\text{Flux} = DC_b/\Delta g \qquad (1)$$

The mass per unit area of resin $M_a$, after time, t, is then:

$$M_a = DC_b t/\Delta g \qquad (2)$$

$$C_r = M_a/\Delta r \qquad (3)$$

After a given time, the concentration in the resin layer, $C_r$, can be measured and the concentration in the solution can be quantified by $$C_b = C_r \Delta g \Delta r/Dt \qquad (4)$$

Clearly therefore the longer the device 1 is immersed in liquid 7 the more metal will be accumulated in the resin 4. Furthermore the ratio of the concentration of metal in the resin layer to metal in solution will increase as the thickness of the resin and gel layers are decreased.

Assuming a typical value of D of $10^{-5}$ cm$^2$ s$^{-1}$, for a 24 hour immersion, a gel layer 2 thickness of 0.1 cm and a resin layer thickness of 0.01 cm, the concentration in the resin layer will be 864 times greater than the concentration in the bulk solution. The device therefore provides a large concentration enhancement for relatively short immersion times.

Equations (1)–(4) depend on the assumption that the thickness of the diffusive boundary layer 8 is negligibly small. This would not be the case for the bottom waters of stratified lakes or deep sea locations where estimates of the boundary layer thickness above the sediment are typically about 1 mm. Increasing the gel layer thickness does overcome this problem but sensitivity is reduced. However in faster moving waters such as the surface waters of lakes and seas the boundary layer thickness $\delta$, should be much smaller: estimates suggest a range of 0.1–001 mm may be appropriate. If the gel layer 2 is 1 mm thick, variation in $\delta$ between 0.1 and 0.01 mm could at most result in a change in flux to the ion exchange resin of 10%. Therefore by ensuring that the gel layer 3 is sufficiently thick, it can in principle control the mass transfer of metal ions irrespective of changes in the velocity of water in the bulk solution.

Diffusive Boundary Layer thicknesses in rivers, streams and piped effluents can be expected to be much smaller than in seas or lakes and so measurements in these situations should be completely independent of flow smaller membrane thickness down to 0.1 mm may then be employed.

The illustrated device is used to obtain a time averaged mean for the concentration of the metal ion $M^{n+}$ in a particular environment. Providing that the thickness of the gel layer 3 is significantly greater than that of the diffusive boundary layer, the concentration factor increase provided by resin 4 in a given time may be calculated theoretically. Thus if the device is immersed for that time and the concentration of the metal ion in the resin is then measured, the average concentration of the metal ion in the surrounding liquid during the time interval considered may be determined.

The determination of the amount of complexed metal ion in the ion exchange resin may be affected, for example, by extracting the resin with an acid (to regenerate the H$^+$ form of the resin) and analysing the obtained solution by standard techniques (e.g. atomic adsorption spectroscopy or Inductively Coupled Plasma Mass Spectrometry (ICPMS)) to determine the concentration of the ion.

Alternatively the ion concentration may be determined by beam technique such as proton microprobe employing MeV-proton-induced X-ray emission (PIXE) to analyse, to submillimetre resolution, the concentration of metal ion at different positions along the layer of ion exchange resin. It is therefore possible to fix the device in position in an aqueous environment (with gel layers 2 and 3 extending vertically) and after a given period of time retrieve the device and analyse the resin layer to determine the ion concentration at different depths.

Radioactive ions may be measured by conventional counting procedures. If the resin 4 is sufficiently selective for a single ion, multi-channel counting is not necessary.

Figure 3:
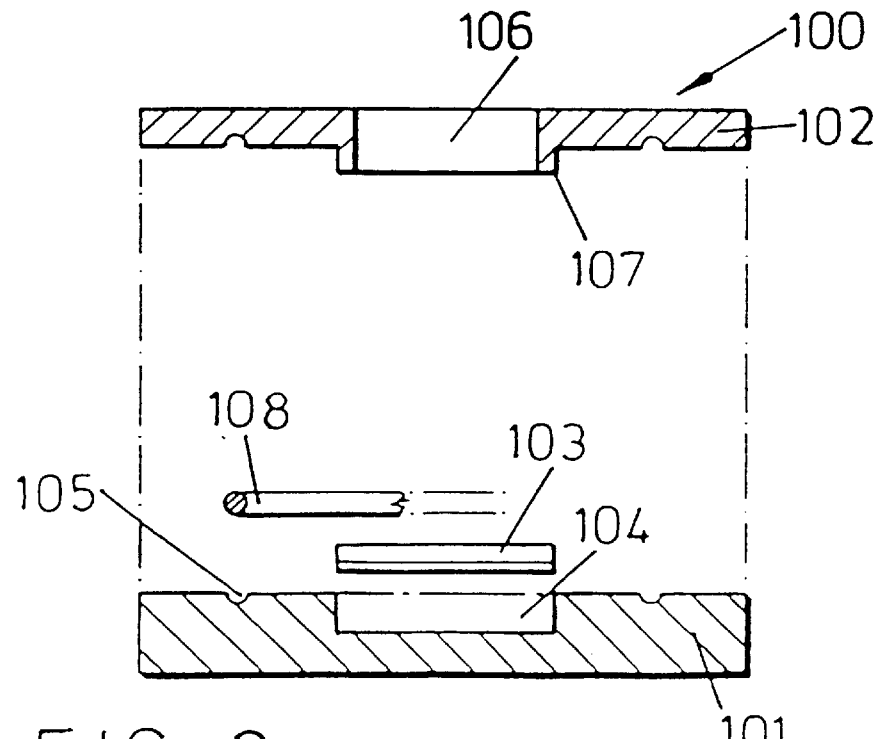
FIG. 3 is an exploded perspective view of a first embodiment of device in accordance with the invention.

Reference is now made to FIG. 3 which is an exploded perspective view of an embodiment of a probe device in accordance with the invention. The device 100 shown in FIG. 3 comprises a base plate 101 and a cover plate 102 between which is located a gel layer assembly 103.

In more detail, the base plate 101 has a central circular recess 104 which is of the same diameter as the (circular) gel layer assembly 103 which (in the assembled device) seats in recess 104. Further provided in base plate 101 is a circular O-ring groove 105 which locates around recess 104.

Cover plate 102 has a central circular aperture 106 of a diameter slightly less than recess 104. An annular flange 107 bounds aperture 104 on the lower surface of the cover plate and has an outer diameter equal to that of recess 104.

The gel layer assembly 103 is similar to that illustrated in FIG. 1 and includes a layer of an ion exchange resin at one face thereof.

To assemble the device, the gel layer assembly is positioned in recess 104 with the resin face adjacent to the bottom of the recess. An O-ring 108 is positioned in groove 105 and then the cover plate is located in position such that flange 107 locates within recess 104 with the lower face of the flange engaging the marginal edge of the gel layer assembly.

Any suitable means may be used for holding the base plate 101 and cover plate 102 together.

If desired a thin filter (thinner than the gel layer) may be positioned on the front of the gel to prevent clogging by impurities. In the alternative, the gel layer may be replaced by a filter as the membrane.

Figure 4:
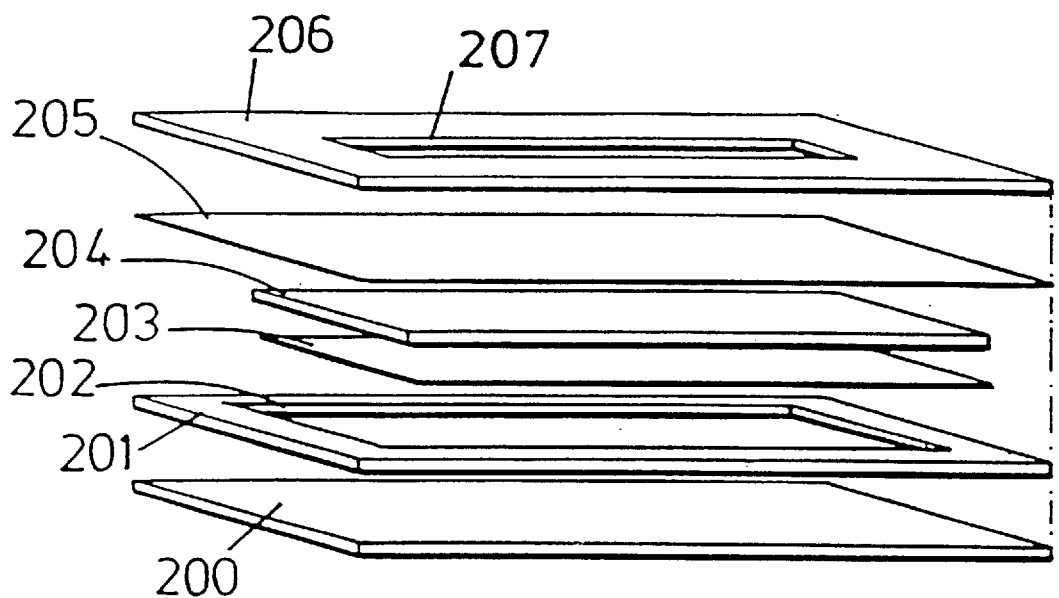
FIG. 4 is an exploded perspective view of a second embodiment of device in accordance with the invention.

FIG. 4 is an exploded perspective view of a further embodiment of a device in accordance with the invention which comprises a backing plate 200 (e.g. 15 cm×5 cm) juxtaposed to a spacer 201 having a rectangular aperture 202 as shown. A resin layer 203 (binding layer) and a gel layer 204 each have a length and a width equal to that of aperture 202 and locate therein. The combined thickness of the layers 203 and 204 is slightly greater than that of spacer 201. Overlying gel layer 204 is a filter 205 as shown, above which is a retaining plate 206 having a window 207 through which the filter 205 may be exposed to an aqueous environment.

The whole assembly may be clipped or screwed together. Since the combined thickness of gel layer 204 and resin layer 203 is greater than that of spacer 201, the flexibility of these layers provide a seal.

Figure 5:
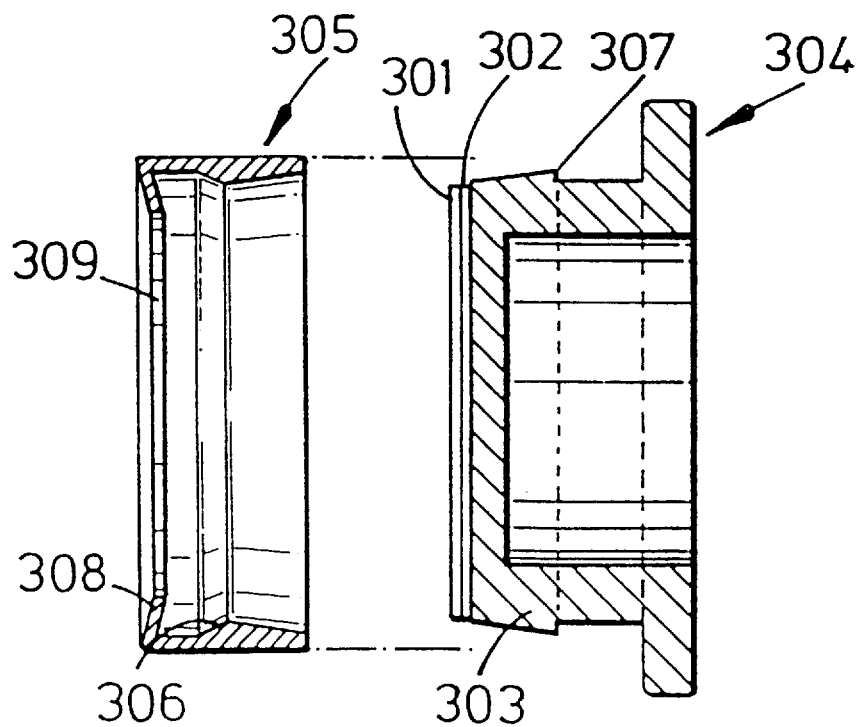
FIG. 5 is an exploded perspective view of a third embodiment of device in accordance with the invention.

FIG. 5 diagrammatically illustrates a further embodiment of device in accordance with the invention. In this arrangement, a gel layer 301 is juxtaposed to a binding layer 302, the latter being positioned on a face of a generally cylindrical body 303 of a plastics mounting arrangement 304. A plastics ring 305 is adapted resiliently to clip onto the body 303 so as to be retained by retaining slopes 306 of the clip engaging against lugs 307 of the body. With the ring so mounted, an in-turned edge 308 of the ring 305 acts against the gel layer 301. The flexibility of the plastic ensures a forward pressure on the gel and ensures a good seal at the back of the gel. The gel presses against the edge 308 which is also flexible and thus provides a seal at the front of the gel, which is exposed to the environment through the aperture 309 of ring.

To illustrate the method of the invention for measuring concentration of metal in water, devices of the type shown in FIG. 3 were used. The devices each comprised a 10.5 cm diameter, 1.3 cm total thickness perspex disk containing layers of gel and resin. The gel was 0.4 mm thick and was exposed through a 5.0 cm diameter window. The gel used was a polyacrylamide gel which, after casting, had been hydrated in water for at least 24 h to ensure dimensional stability before use. The resin (Chelex 100) was embedded in a separate gel (approximately 150 microns thick) as a single plane of approximately close packed beads. To analyse the results of the tests, the gel layer was peeled off, metal was extracted from the resin layer with 1 ml of 2M HNO$_3$ and measured using atomic adsorption spectroscopy. Self-diffusion coefficients for Zn (the metal measured) for the appropriate temperatures were used (Li, Y. & Gregory, S. Geochim. Cosmochim. Acta 38, 703–714 (1974)).

Test 1

Laboratory exposures of the assembly to stirred solutions of ca $10^{-7}$M $Zn(NO_3)_2$, with and without added NaCl (0.5M), showed that the concentration of metal measured in the resin layer could be predicted quantitatively (97–100%) by equation (4).

Test 2

The device was used, in the laboratory, for measurement of Zn in sea water. Assemblies were suspended for different times in a stirred solution of natural sea water (pH7.8) in the laboratory (28° C.). The measured masses of zinc, at various times, are plotted on FIG. 6.

Figure 6:
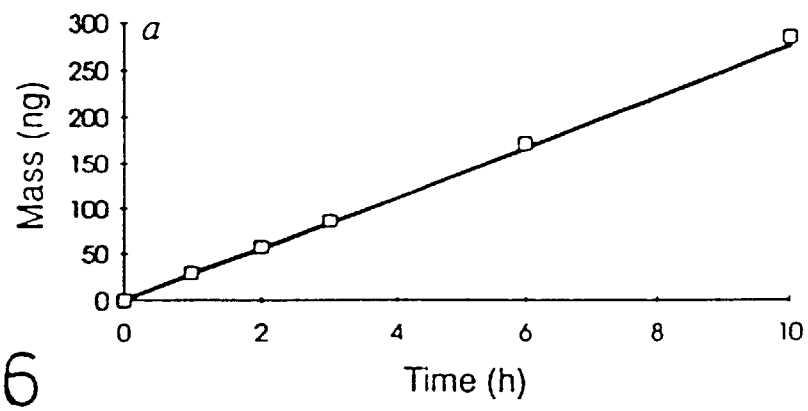
FIGS. 6–8 are graphs representing results of tests carried out with a device in accordance with the invention.

The concentration of labile zinc in the sea water was measured by direct anodic stripping voltammetry to be 31 nM and was used with equation (2) to calculate the straight line which is shown in FIG. 6. The good fit between the experimental data demonstrates the excellent agreement between anodic stripping voltammetry and the results obtained by the device in accordance with the invention in measuring labile zinc in a natural sea water sample.

Test 3

The assemblies having a 0.4 mm gel layer were suspended in sea water (Menai Straits, U.K., Salinity 32‰, 14° C.) for various times. To prevent accumulation of particulates, the assemblies were covered with a 100 micron thick, 0.45 micron pore size Millipore cellulose nitrate membrane.

Figure 7:
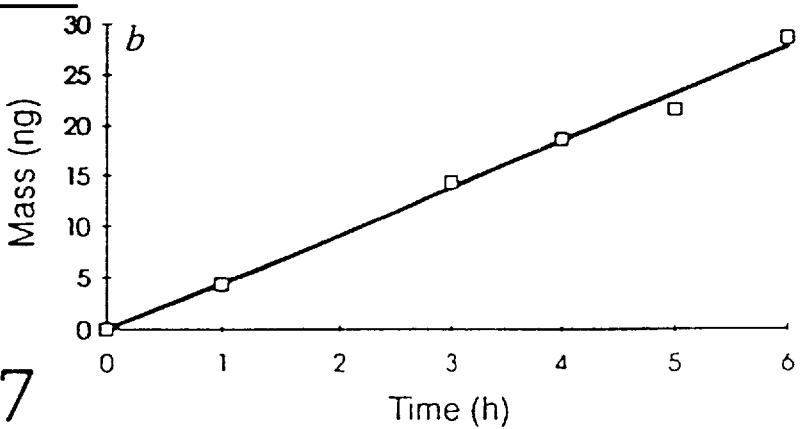

The results are shown in FIG. 7.

Varying the time of in situ immersion in sea water, resulted in the measured mass of zinc increasing linearly with time. As the tidal current varied from 0 to ca 4 knots during this time, the thickness of the Diffusion Boundary Layer will also vary. Consequently the linear response indicates that the gel thickness is dominating the control of mass transport confirming the assumption that the DBL is negligible.

The mean concentration from these measurements was very reproducible at 11.9±0.4 nM as compared to 26.5±2.8 nM from 7 samples taken at hourly intervals and measured by anodic stripping voltammetry after acidification to pH 2 and exposure to ultra-violet irradiation. A difference is to be expected when it is considered that the device in accordance with the invention only measures labile species and therefore will exclude kinetically inert organic species and large colloids.

Test 4

To investigate further the effect of the gel layer, assemblies of different gel thicknesses, covered by 100 micron thick filters, were exposed to sea water for 320 minutes.

Figure 8:
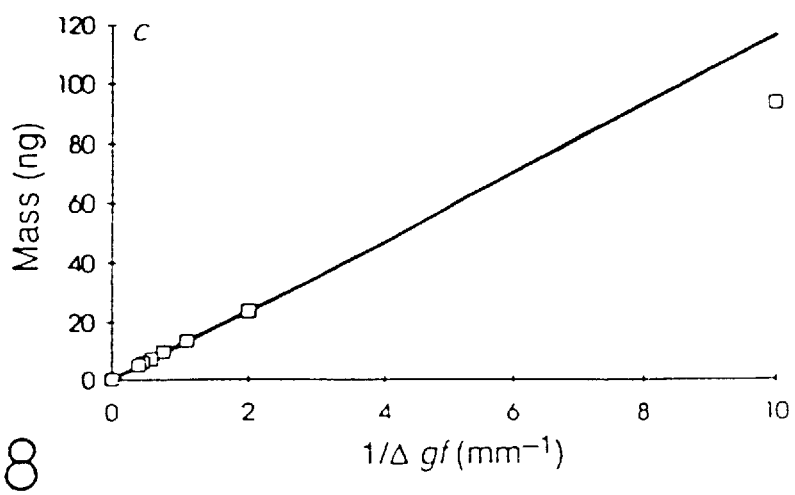

The results are shown in FIG. 8 which is a graph of measured mass of zinc in the receiving resin against the reciprocal of the combined gel and filter layer thickness (1/Δgf).

When the mass per unit area, $M_a$, is found to be inversely proportional to the combined thickness of the gel and filter layer, as for most of the combined thickness used in FIG. 8, equation (2) is fulfilled, verifying the assumption that the diffusive boundary layer thickness, DBL, is negligible. Where there is a deviation from linearity, as is the case when only a 100 micron filter was used, equation 5, which incorporates the thickness of the DBL, $\Delta_{dbl}$, is applicable.

$$M_{a(m)}=DCbt/(\Delta gf+\Delta_{dbl})$$

$M_{a(m)}$ is the measured mass per unit area when the DBL thickness is not negligible. For the 100 micron filter case in FIG. 8, the value of Ma which would have been obtained if $\Delta_{dbl}$ was negligible is given by the value of the extrapolated line at the appropriate value of 1/Δgf. As D,$C_b$ and t must remain constant in the same measured experiment, equations (2) and (5) may be combined to give equation (6) from which $\Delta_{dbl}$ may be calculated.

$$M_{a(m)}(\Delta gf+\Delta_{dbl})=M_a \Delta gf$$

For this particular experiment the effective mean thickness of the DBL, $\Delta_{dbl}$, was calculated to be 30 microns.

What I claim is:

1. A probe device for use in measuring quantities of a component in a liquid environment, the device comprising means providing a diffusion pathway, the pathway being or containing a liquid and having a length of at least 0.1 mm, a liquid impermeable barrier such that only one end of the diffusion pathway contacts the liquid environment, and a material in contact with the diffusion pathway and arranged to bind the component which has diffused along said pathway characterized in that said material is an immobile material provided as a layer.

2. A device as claimed in claim 1 wherein the diffusion pathway has a length up to 10 mm.

3. A device as claimed in claim 2 wherein the diffusion pathway has a length up to 5 mm.

4. A device as claimed in claim 3 wherein the diffusion pathway has a length of 0.2 mm to 5 mm.

5. A device as claimed in claim 4 wherein the diffusion pathway has a length of 0.4 mm to 2.5 mm.

6. A device as claimed in claim 1 wherein the diffusion pathway is provided by a membrane.

7. A device as claimed in claim 6 wherein the membrane is a gel.

8. A device as claimed in claim 7 wherein the gel is a polyacrylamide gel.

9. A device as claimed in claim 6 wherein a filter is provided over the face of the membrane remote from said material.

10. A device as claimed in claim 6 wherein the material for binding the component is incorporated in the membrane.

11. A device as claimed in claim 6 wherein the material for binding the component is provided as a separate layer to the membrane and is juxtaposed thereto.

12. A device as claimed in claim 6 wherein the membrane is a filter.

13. A device as claimed in claim 1 comprising a solid member having a plurality of apertures extending through the thickness thereof, said apertures containing a liquid for providing the diffusion pathway, and means across which the component may pass for retaining the liquid in the apertures, the device being such that movement of the liquid in the apertures is prevented at each end thereof.

14. A device as claimed in claim 1 wherein the material for binding the component is a particulate material in a layer.

15. A device as claimed in claim 1 wherein the material for binding the component is an ion exchange material.

16. A device as claimed in claim 15 wherein the ion exchange material is a cationic exchange resin.

17. A device as claimed in claim 1 wherein the material is iron oxide.

18. A device as claimed in claim 1 wherein the material comprises an immobilized complexing agent.

19. A device as claimed in claim 1 wherein the material is anionic exchange resin.

20. A device as claimed in claim 1 wherein said material is for binding organics.

21. A device as claimed in claim 1 wherein said layer of material has a thickness of 10 to 1000 micrometers.

22. A device as claimed in claim 21 wherein said layer of material has a thickness of 10 to 200 micrometers.

23. A method of determining the amount of a component present in a liquid environment comprising providing a device as claimed in claim 1 in the liquid environment and subsequently analyzing said material to determine the amount, or a representation of the amount, of said component therein.

24. A method as claimed in claim 23 wherein the liquid environment is an aqueous environment.

25. A device as claimed in claim 1 wherein the liquid of the diffusion pathway is water.

* * * * *